Nov. 29, 1932. W. H. BRAKE Plant Pat. 47
PECAN
Filed March 1, 1932
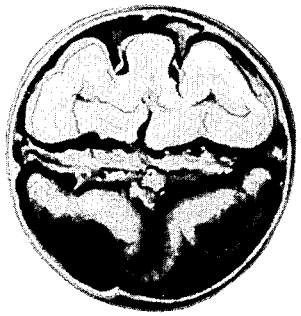
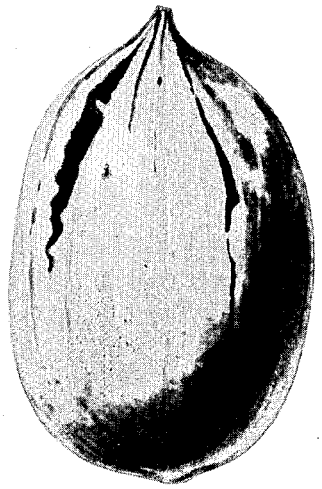
INVENTOR
William H. Brake
By Orville M. Kile
PLANT PATENT AGENT Patented Nov. 29, 1932

Plant Pat. 47

UNITED STATES PATENT OFFICE

WILLIAM H. BRAKE, OF ROCKY MOUNT, NORTH CAROLINA

PECAN

Application filed March 1, 1932. Serial No. 596,128.

My invention relates to improvements in edible, commercial pecans of the type known as "paper-shell," in which the qualities of thickness of shell, plumpness and flavor of the kernels, tendency of the kernels to crack out whole, and the productiveness of the trees as well as resistance to disease, are important features which give one variety preference over another. The principal objects of my invention are to provide a pecan having the principal good qualities of the well-known Schley variety combined with the additional characters of a much thinner shell, greater productiveness, and greater resistance to disease.

My new variety originated as a seedling, being one of five trees produced from as many pecan nuts planted on my father's farm near Rocky Mount, North Carolina. Only one of these five trees produces nuts of the superior type described herein, the product of the other four trees being far different. All five of the original nuts planted came from a single tree then growing in or near Raleigh, North Carolina. As these trees grew into producing size, the superior qualities of the one outstanding tree of this group of five trees was noted by me, and after a few seasons of observation and comparison with other known varieties of pecans I took steps to reproduce this new variety asexually. A small stock of my new variety has now been grown and will soon be offered for sale.

The accompanying illustration shows a full side view of this new variety and a cross section.

The following is a more detailed description of my new variety of pecan:

Size of nuts; medium, the full length ordinarily being 1⅜ to 1½ inches; form regular and not having flattened areas except at the blossom end—a cross section perpendicular to the axis of the nut and midway between ends being practically a circle; the base of the nut where attached to the hull is notably smooth and rounded rather than pointed; color of the exterior surface grayish brown with a few streaks of reddish brown on the half of the nut nearest the pointed end, in these respects notably differing from the well-known Schley variety which when grown nearby is not only flattened and irregular in shape but is liberally splashed and streaked with red and even purple: the kernels are plump and of good texture and flavor; in shape they are rounded and relatively short as compared with the long narrow kernels of the Schley variety; in color the kernels are somewhat lighter than the kernels of the Schley variety grown under similar conditions of soil and climate, the surface of the kernels being slightly indented and marked by irregular slightly depressed lines whereas in the Schley variety the surface of the kernels is smooth except for a single longitudinal and rather deep indentation in each quarter: the shell is extremely thin, being approximately 60 to 70 percent as thick as the shell of the Schley variety on the average; the kernels hold together well and readily crack out as full halves.

The foliage remains on the trees of this variety somewhat later in the fall than on trees of other varieties grown nearby under similar conditions of soil and climate. The nuts of this new variety mature a little later than the Schley and have the very desirable quality of not falling to any important extent until practically all the nuts on a tree are ripe and ready to harvest.

This variety makes a good crop every year as contrasted with many other varieties which fail to fruit in many seasons; also each nut practically always contains a good kernel, a point of importance not only in weight of total yield but in consumer satisfaction.

Observations to date indicate greater freedom from such diseases as leaf scab and mildew, also rarer insect attacks.

I claim:

A variety of pecan as herein shown and described, characterized particularly by its extraordinarily thin shell, its regularity of shape, its plump kernels of good flavor, its superior cracking-out qualities, its regularity and sureness of fruiting and its relative freedom from diseases.

WILLIAM H. BRAKE.